United States Patent [19]
Kauvar et al.

[11] Patent Number: 5,338,659
[45] Date of Patent: Aug. 16, 1994

[54] METHOD FOR DETERMINING ANALYTE CONCENTRATION BY CROSS-REACTIVITY PROFILING

[75] Inventors: Lawrence M. Kauvar, San Francisco, Calif.; Stuart M. Ambler, Longmont, Colo.

[73] Assignee: Terrapin Technologies, Inc., South San Francisco, Calif.

[21] Appl. No.: 678,849

[22] Filed: Apr. 2, 1991

[51] Int. Cl.$^5$ .................. C12Q 1/00; G01N 33/53; G01N 33/566; G01N 33/563
[52] U.S. Cl. ........................ 435/7.1; 435/7.92; 435/7.93; 436/501; 436/512; 436/815; 436/816; 436/817; 436/901
[58] Field of Search ............. 435/7.1, 7.92, 7.93; 436/501, 512, 815, 816, 817, 901

[56] References Cited
PUBLICATIONS

Davis et al (1980) Microbiology, Harpert Row, New York pp. 298-306, 314-323.
Musumarra et al (1987) J Analyt Toxicol 11:154-163.
Clark W., *The Experimental Foundations of Modern Immunology* (1980), John Wiley and Sons, New York, pp. 81-92.
Van Emon et al., "Analytical Methods for Pesticides and Plant Growth Regulators: Advanced Analytical Techniques," Sherma, J. ed., Academic Press, New York, (1989) pp. 217-263.
Vanderlaan et al., *Environ. Sci. Technol.* (1988) 22(3):247-254.
Newsome, *J. Assoc. Offic. Anal. Chem.* (1986) 69:919-923.

*Primary Examiner*—Esther L. Kepplinger
*Assistant Examiner*—David R. Preston
*Attorney, Agent, or Firm*—Morrison & Foerster

[57] ABSTRACT

The precision of identification of analyte composition in a sample, where the possible analytes cross-react with specific binding reagents, is enhanced by applying pattern recognition techniques. Samples to be tested are reacted with a panel of specific binding reagents reactive with the set of analytes to be tested to obtain a pattern of reactivity with respect to each analyte at a given concentration. This results in a databank of "CRIM profiles" for known concentrations of each analyte. This databank is stored in a computationally accessible form, which then can be matched against CRIM patterns obtained by testing unknown samples. In one embodiment, each CRIM pattern obtained is plotted as a single point in n-dimensional space, wherein n represents the number of specific binding reagents in the panel. Because a different CRIM profile as a function of concentration is obtained with each analyte, a pattern of points in n-dimensional space can be constructed for various concentrations of each individual member. Mathematical techniques can be used to project the pattern from n-dimensional space to reduce dimensionality. The location of a point yielded by a sample of unknown concentration can then be matched against those for predetermined known compositions to determine best estimate.

26 Claims, 4 Drawing Sheets

METHOD FOR DETERMINING ANALYTE CONCENTRATION BY CROSS-REACTIVITY PROFILING

TECHNICAL FIELD

The invention relates to analysis of unknown samples using specific binding reagent-based assays. More specifically, the invention concerns the use of pattern recognition, wherein patterns are determined by reactivity of known samples with panels of specific binding reagents, to identify the analyte composition of unknown samples. The method can also recognize classes of analytes.

BACKGROUND ART

Immunoassay and related techniques have become the norm for determination of various analytes in biological samples. A variety of formats designed to simplify and improve the accuracy of these tests is available in the art, and the number represented by this variety of formats is very high.

The success of these assays rests in the ability to provide specific binding reagents, usually antibodies or fragments of antibodies, which are highly specific for the target analyte with respect to additional possible components of the sample. For example, there are a large number of assays on the market for pregnancy which rely on the detection of human chorionic gonadotropin (HCG) in urine. These assays are capable of HCG detection because the antibodies provided, which are immunoreactive with HCG, do not react to any detectable extent with other urinary components.

In certain other contexts, however, it is desired to analyze samples for analytes which are members of groups that are cross-reactive with antibodies prepared against any one of them, and any or a number of which may be present in the same sample. One example of this problem relates to the efforts to determine pesticides and herbicides in the environment, since many of these materials are structurally similar. See, for example, van Emon, J. N., et al., in "Analytical Methods for Pesticides and Plant Growth Regulators: Advanced Analytical Techniques," Sherma J. ed., Academic Press, New York, 1989, pp. 217-263; Vanderlaan, M., et al., *Environ Sci Technol* (1988) 22:247-254; Newsome, W. H., *J Assoc Offic Anal Chem* (1986) 69:919-923.

Typically, it will not be known for certain which of the several members of a particular class of pesticides, for example the carbamate pesticides, will be present in the environment; in addition, degradation products of the pesticide actually applied may also cross-react with a purportedly specifically immunoreacting antibody or other binding agent. Thus, it will not be possible, in a simple single antibody assay to obtain a reliable picture of the composition of the sample. Indeed, the results of such assays are often given in terms of "equivalents" of a particular identified member of the class to which the antibody, for example, has been prepared. In addition to the cross-reactivity of the possible analytes for any specific binding reagent created against one of them, the concentration ranges of these compounds are very low in typical determinations, typically 10-100 nM, or in the parts per billion range. At these low concentrations, problems of crossreactivity with more abundant materials are particularly troublesome.

Because of the cross-reactivity discussed above, it is difficult to make a definitive determination of analyte concentration. For example, suppose an antibody has 100 times the affinity for analyte B as for analyte A. It would not be possible to distinguish, using a single determination with that antibody, a 50 nM concentration of analyte A from a 0.5 nM concentration of analyte B. Various mixtures of A and B would also react in a quantitatively identical manner. Thus there is no mechanism to use a single antibody for assaying samples that contain mixtures of various structurally similar analytes.

The present invention overcomes these difficulties by utilizing mathematical pattern recognition techniques applied to panels of binding agents with overlapping specificities. Once a set of standard binding patterns for target analytes is determined, more reliable determination of analyte composition in experimental samples becomes possible with concomitant improvement in the accuracy of analyte quantitation.

DISCLOSURE OF THE INVENTION

Methods are provided which permit determination of analyte composition of samples where the potential analytes are closely structurally related. These methods take advantage of pattern recognition techniques and the manipulation thereof to provide detailed information as to sample composition.

In one aspect, the invention is directed to a method to determine the analyte composition of a sample, which method comprises contacting the sample with a panel of specific binding reagents each of which is reactive with the members of a class of suspected analytes. A profile of reactivity is obtained for the sample, and this profile is then matched with a predetermined profile of standard known compositions.

In another aspect, the invention is directed to a method to obtain the predetermined profile for various known analyte compositions which comprises contacting a set of predetermined compositions with a panel of n specific binding reagents reactive with these analytes, wherein n is preferably 2-10, and plotting the obtained profile in n-dimensional space for each composition. In still another aspect, the invention is directed to the composition pattern so determined.

In still another aspect, the invention is directed to the use of multi-parametric statistical techniques to define which of the n dimensions have the greatest information content relative to the assay and thus permits selection of the minimum number of characteristics (dimensions) to be measured.

Modes of Carrying out the Invention

Figure 1A:
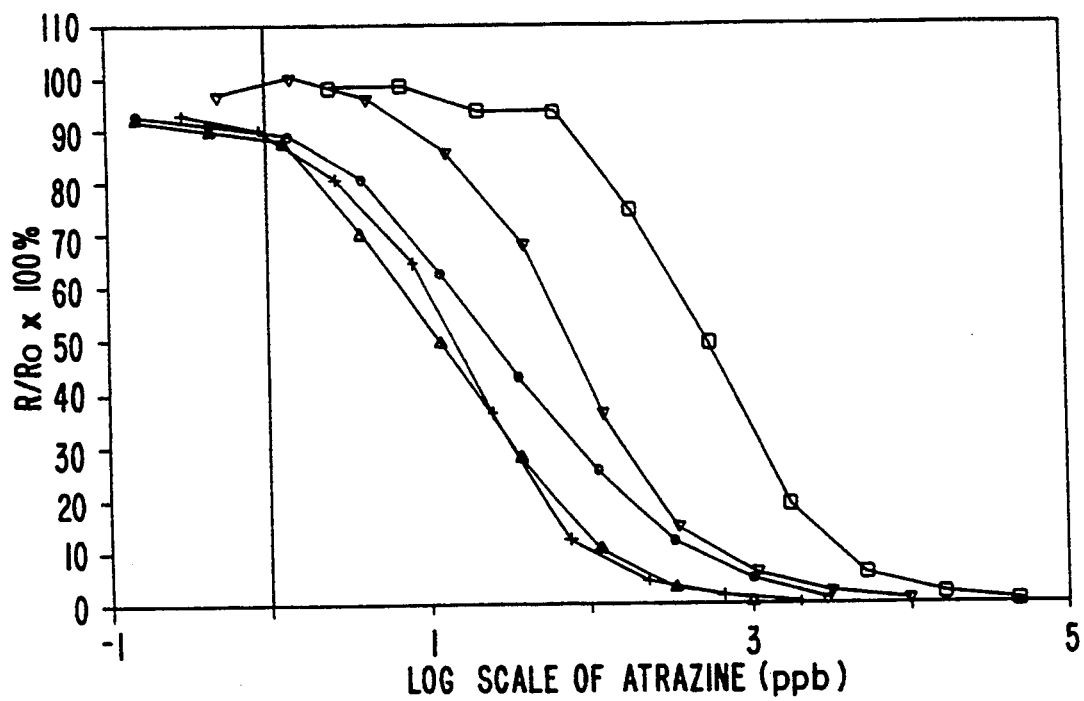
FIG. 1A shows patterns of inhibition of binding of a series of monoclonal antibodies to immobilized atrazine as a function of concentration of related antigens in solution.

The methods of the invention improve the reliability of determination of analyte compositions in impure samples especially wherein the analytes suspected of being contained in the samples are relatively closely related structurally. By "determination of analyte composition" is meant the ascertainment of the concentration level of each of a number of possible suspected analytes. Situations wherein determination of analyte composition is meaningful include those wherein a number of structurally related materials can be used for similar purposes or where these materials are manipulated in such a way so as to result in their occupying similar environments. For example, many herbicides and pesticides are homologs or analogs of each other, as are their degradation products. Exemplified below is the case of various triazine derivatives, all of which are useful as herbicides.

Other examples of such groups include families of substances which might be found in biological fluids or tissues (useful in clinical analysis of biological samples). In general, these families fall into three categories. First, naturally-occurring substances which may be at enhanced or reduced elevation due to clinical conditions or their direct administration, such as steroids, protein hormones, or metabolites are of interest clinically. Second, artificial materials which are designed for therapeutic purposes, such as beta-blockers, chemotherapeutic agents, prostaglandin inhibitors, and the like, can be monitored. Third, families of various illicit drugs can be detected and distinguished for forensic purposes.

The series of starting reagents and products in a series of reactions leading to the synthesis of a desired product can also be measured (useful in online quality control routines). The method of the invention for such measurement is particularly useful in instances where the materials are synthesized in families and the products represent concomitantly produced and subsequently separated fractions. Typical examples include textile dyes, PCB's used in insulators, and detergents. In all manufacturing, moreover, competing side reactions often produce members of the same family which are structurally similar and need to be distinguished from the desired product.

Analyses related to degradation of various substances in the environment can also be determined (as in the assessment of persistence of environmentally important substances).

The methods of the invention depend on the reactivity of the analytes with specific binding reagents. Because the analytes are structurally similar, considerable cross-reactivity is expected, and, indeed, the necessity for and practicality of the method of the invention depends on this cross-reactivity. While the specific binding reagent is most commonly an antibody, typically a monoclonal antibody, this is not a requirement, and any substance which is determined to react generally with the group of analytes whose presence, absence or quantity is to be determined is usable in the method of the invention. Antibodies, including, for example, single chain antibodies and recombinantly produced antibodies, can be used per se, or as immunologically reactive fragments thereof, as is well understood in the art. The use of, for example, Fab, Fab' or F(ab')$_2$ fragments is often convenient in specific binding assays. Any binding reagent interaction which provides suitable cross-reactivity can be used, such as enzyme-substrate or enzyme-inhibitor binding, ligand-receptor binding, or binding to an affinity reagent such as the paralogs described in U.S. Pat. No. 4,963,263 incorporated herein by reference.

Similarly, the choice of specific assay format which detects the binding of the specific binding reagent to the analyte group is optional. The reactivity of the sample to be tested and the production of a standard set of data points for various analyte compositions can be determined in either a direct or competitive format. For example, the specific binding agent can be labeled and the binding to antigen detected by precipitating the resultant complex and determining the amount of label in the precipitate. Alternatively, and more conveniently, the specific binding reagent is coupled to a solid support and the candidate analyte allowed to compete with a similar analyte of known binding capacity. Additional methods for conducting assays designed to detect and measure binding of a specific binding reagent to the analytes in a particular group are disclosed in U.S. Ser. No. 447,009, filed 6 Dec. 1989, and incorporated herein by reference. Methods for design of specific binding reagents are also found in U.S. Pat. No. 4,963,263 and its continuation-in-part, U.S. Ser. No. 429,721, filed 31 Oct., 1989, both incorporated herein by reference. Alternative protocols will be immediately apparent to practitioners of immunoassays or other specific binding assays.

However the level of binding to specific binding reagent is determined, a profile for a panel of specific binding reagents is determined for a series of known analyte compositions. The simplest such compositions, and those typically used to obtain the standard pattern, are samples containing only single member analytes at a range of concentrations. The standard plot ultimately obtained from these control data points permits detection of single analytes by correlation with known positions. Calculation of plot positions for mixtures permits their identification by similar matching.

In essence, the method of the invention comprises comparing a cross-reaction immunoassay (CRIM) profile of a sample to be tested with a predetermined plot of CRIM profiles obtained from samples of known analyte composition. By "CRIM profile" is meant a pattern of reactivities across a panel of specific binding reagents with respect to a single fixed analyte composition. (Although the term "CRIM" profile is derived from "cross-reactive immunological materials," as set forth above, the specific binding reagent need not necessarily be an antibody.

In order to avoid confusion and the implication of this limitation, the profiles will also be called "cross-reactivity of specific binding reagents, or CRSBR, profile.") In a typical CRIM or CRSBR profile useful in the invention, the reactivity of a sample with a panel of 2–10, preferably 4–6, different specific binding reagents is determined. As will be apparent from the example below, each composition will have a characteristic CRIM or CRSBR profile across the panel. Larger numbers of members of the panel provide greater refinement of the assay; smaller numbers of members of the panel are more convenient. The choice of the number of members of the panel is arbitrary, depending on the level of fine tuning desired in the assay; the mathematical techniques disclosed herein permit selection of the most meaningful panel members and can be used to reduce the number of binding agents needed in the profile.

In obtaining the profiles at various concentrations, the simplest conceptual approach provides this series of profiles by direct measurement of the inhibition values at various known analyte concentrations. However, additional profiles can be interpolated using the curves obtained by plotting % inhibition vs. analyte concentration.

Mathematical Processing

The profiles obtained for the individual standard compositions to be compared to unknown samples are then subjected to computational techniques which permit the comparison of the standard profiles with those of unknowns, a process not readily performed by hand.

In the simplest form of application of these pattern recognition techniques, each CRIM profile is plotted as a point in n dimensions, wherein n is the number of binding agents in each panel.

For example, one might use a panel containing six different binding agents which are monoclonal antibodies. These antibodies are assumed to be cross-reactive with, for example, ten members of a class of analytes $A_i$ wherein A represents the analyte and i is an integer of 1–10. One of these analytes, $A_1$, for example, might be chosen as a labeled competitor to determine profiles of competition for binding at various concentrations of itself and of the remaining analytes. Using a set concentration of labeled $A_1$, the percent inhibition, for example, is determined with respect to binding each antibody in the panel at various concentrations of $A_1$–$A_{10}$.

For each analyte, $A_i$, at one concentration, then, there are six data points which are percentages of inhibition with respect to labeled $A_1$ for binding to the various antibodies in the panel. These percentages are then treated mathematically as defining the location of a single point in six-dimensional space where the first dimension describes the percent inhibition with respect to the first antibody, the second dimension describes the percent inhibition with respect to the second antibody, and so forth. Points are thus determined representing the various concentrations of $A_1$, $A_2$, $A_3$ . . . $A_{10}$.

As a six-dimensional plot is not readily visualized, known mathematical techniques, such as those described by D. L. Massart, et al., "Chemometrics: A Textbook" (1988) Elsevier, (N.Y.), can be used to project the six-dimensional array onto a two-dimensional surface or other surface of lower dimensionality. This series of points in two-dimensional space can then be used to visualize comparisons of the profile obtained using an unknown sample with the profiles of standards to identify the composition of the sample. Of course, as the six-dimensional space can be handled mathematically, there is no requirement for the projection in order to match the data point generated by the samples with those in the set of reference points.

Choosing a projection does, however, provide the additional benefit of rank ordering the antibodies with respect to their utility for CRIM. The more nearly perpendicular the projection plane is to an axis in the six dimensional space, the greater is the loss of that component's information content in the projection. Since factor analysis generates an optimal plane for preserving the scattering aspect of that information, the relative importance of the antibodies in this regard is readily determined. This knowledge may be usefully applied, for example in reducing the number of antibodies in the panel.

In the example described below, it was found that reliable estimates could be obtained for compositions of an unknown sample in about 85% of the cases using this rather simple mathematical approach. Improved results were obtained by applying methods to distinguish between data points which are of significance from those which are relatively meaningless.

In effect, weighting factors for the various members comprising the profile can be introduced to account for the fact that those concentrations which represent inhibition of binding on the linear part of the standard curve are more informative than those in the asymptotic parts of the curve at very low or high inhibition. These factors are applied when the data are treated by "variance analysis." In this technique, in general outline for this example, the value represented by the dimension corresponding to each of the six monoclonal antibodies in the panel is compared separately with the corresponding value for the corresponding antibody in the unknown sample, rather than as a totality of the n-dimensional result for all six antibodies.

For example, the observed inhibition value for antibody #1 implies a corresponding concentration for analyte $A_1$, and a different corresponding concentration for analyte $A_2$, etc. Antibody #2 similarly generates a family of predictions, and so forth. For the correct choice of analyte, the individual predictions of the six antibodies will agree more closely than for an incorrect choice of analyte. This approach to profile identification is a form of variance analysis, normally used to compare independent estimates made in different laboratories or methods of determination. Calculation of variances can be easily modified to weight the predictions by a factor representing the reliability of the data, as judged by the variance in the data set used to construct the standard curve. This procedure is referred to herein as "weighting the results."

This mathematical technique, as described by Mandel, "The Statistical Analysis of Experimental Data" (1984) Dover, provided sufficient weighting of the significant binding data to provide a clear result in 95% of the cases.

Finally, neural net systems can also be used, wherein adjustment factors arise implicitly in the process of training the net's input/output characteristics using standards. The systems are outlined, for example, in Hartz, J. A., et al., *Introduction to the Theory of Neural Computation* (Addison Wesley, Santa Fe Institute Series on Complex Systems, 1991); *Parallel Distributed Processing*, 2 vols. (D. E. Rumelhart and J. L. McClelland, eds., MIT Press, 1986); or *DARPA Neural Network Study* (Armed Forces Communication and Electronics Association Int'l Press, 1988).

The high reliability of analyte identification achieved through the use of small panels of binding agents that have only moderate intrinsic specificity for the compounds is unexpected from prior art binding assays wherein enormous effort has been expended to achieve higher intrinsic specificity. The method of the Invention is thus useful not only for improving the reliability of existing assays, but also for extending the scope of immunoassay technology by facilitating the isolation of suitable antibodies, for example, from recombinant libraries.

Packaged Assays

The reagents and software for use in the assays of the invention could conveniently be packaged to permit rapid and convenient assay of complex samples in situations where various members of a class of compounds may be present, such as in those situations set forth above. A typical kit for such an assay would include the members of a panel of binding reagents, preferably coupled to a solid support, along with labeled competitor and a means for detection of the label. Suitable labels include radioactive isotopes, fluorescence emitters, and enzymes. Alternatively, the binding agents, such as antibodies, may be supplied in labeled form and a competitive analyte linked to solid support. For direct conduct of the assay, a sandwich format could be used wherein antibody-coated solid supports are reacted with sample and then treated with a second antibody bearing label.

The values obtained in the reaction of the binding agent panel with the sample are then compared to the reference data bank. Software supplied with the packaged reagents permits entry of the relevant results obtained from the sample and comparison to the reference panel. The nature of the software will depend on the particular mathematical processing selected, as described above.

The following example is intended to illustrate, but not to limit, the invention.

Preparation A

Production of Monoclonal Antibodies

Two s-triazine compounds, atrazine and simazine (see Preparation B) were conjugated to keyhole limpet hemocyanin (KLH) using NHS and EDCI (Pierce Chemical Company, Rockford, Ill.) and used to immunize mice, as described by Goodrow, M., et al., *J Agric Food Chem* (1990) 38:990–996. When high titers of anti-s-triazine antibodies were obtained, the mice were sacrificed and the spleen cells were recovered. Fusions of the spleen cells with murine myeloma cells in 50% polyethylene glycol yielded hybridomas which were screened for antibody production using an ELISA assay for binding to immobilized atrazine bovine serum albumin (BSA) conjugates. These conjugates were prepared using a carbodiimide-based protocol.

Positive cultures were cloned by limiting dilution and stable cell lines were cultured in complete medium with 5% fetal bovine serum. Culture supernatants were collected, aliquoted and stored frozen at −20° C.; antibody IgG subtypes were determined using an isotyping kit from Zymed. A panel of 5 monoclonal antibodies reactive at various affinities with seven important s-triazine derivatives were selected. These are AM5C5.3, AM1B5.1, AM5D1.2, and AM7B2.1 from the atrazine immunization and SA5A1.1 from the simazine immunization.

Preparation B

Antigen/Analyte Compositions

A set of 7 triazine analogs was used to illustrate the invention technique. The structures of these analogs, which are commercially available, are shown in Table 1.

TABLE 1

| Triazine Analogs | $R^1$ | $R^2$ | $R^3$ |
|---|---|---|---|
| 1. Atrazine | Cl | Isopropyl | Ethyl |
| 2. Simazine | Cl | Ethyl | Ethyl |
| 3. Propazine | Cl | Isopropyl | Isopropyl |
| 4. Prometon | O—Methyl | Isopropyl | Isopropyl |
| 5. Prometryne | S—Methyl | Isopropyl | Isopropyl |
| 6. Ametryne | S—Methyl | Ethyl | Isopropyl |
| 7. Terbutryne | S—Methyl | t-Butyl | Ethyl |

For conjugation to BSA or KLH via carbodiimide-mediated crosslinking the ethyl group at $R^3$ in atrazine is replaced by —(CH$_2$)$_5$COOH and the chloro group for simazine at position $R^1$ is replaced by —SCH$_2$CH$_2$COOH.

In general, conjugation is to a different carrier for immunization and for screening. This minimizes detection of antibodies in the screen which are raised against the carrier, rather than the desired hapten.

Example 1

Determination of Antibody Specificity

Five monoclonal antibodies obtained as described in preparation A were tested for reactivity with respect to the seven analytes of preparation B. This profiling was conducted using an ELISA format in 96-well microplates. The plates were coated overnight at 4° C. with an atrazine-BSA conjugate. Extraneous protein-binding sites were blocked by 2-hour incubation with 0.5% each of BSA and casein, followed by washing with PBS-Tween (10 mM Na phosphate, pH 7.2, 100 mM NaCl plus 0.05% Tween-20). The antibody to be tested plus varying concentrations of the s-triazine analog to be tested in assay buffer (PBS/Tween plus 0.1% each BSA and casein) were added to the plate in quadruplicate wells. The plates were incubated at room temperature for 2 hours. Bound antibody was quantitated using a secondary alkaline phosphatase-labeled goat antimouse IgG (1:1000) with p-nitrophenol phosphate as substrate (1 mg/ml in 0.1M diethanolamine, pH 10.3; 0.5 mM MgCl$_2$). Endpoint accumulation of reaction product was determined by measuring absorbance at 405 nm with a Vmax microplate reader (Molecular Devices, Menlo Park, Calif.). Inhibition curves were fitted using the Four-Parameter Logistic Program in the software package Soft Max (V.2.01C, Molecular Devices). The reduction in binding of the monoclonal antibodies to the solid phase due to the presence of the s-triazine analog at a particular concentration was expressed as a percentage of optical density of the zero-dose control (R/Ro×100%).

Typical results for atrazine and prometryne are shown in FIG. 1A and B, respectively. As shown in the figure, the inhibition curves over the panel are different for the two analogs. The IC$_{50}$ values (the concentration at which 50% inhibition was obtained) are displayed for all seven analogs against the 5-member antibody panel in Table 2.

TABLE 2

Anti-Triazine Mabs and Their Relative Specificities Against Seven S-Triazines

| Cell Line* | IgG Subtype | IC50 (ppb)** | | | | | | |
|---|---|---|---|---|---|---|---|---|
| | | Atrazine | Simazine | Propazine | Prometon | Prometryne | Ametryne | Terbutryne |
| AM5C5.3 | IgG 2b K | 555.0 | 884.0 | 596.0 | 9700.0 | 3030.0 | 1790.0 | 1330.0 |
| AM1B5.1 | IgG 1 K | 15.5 | 273.0 | 6.7 | 18.4 | 3.2 | 6.6 | 494.0 |
| AM5D1.2 | IgG K | 29.6 | 56.5 | 7.7 | 176.0 | 42.8 | 92.8 | 61.0 |
| AM7B2.1 | IgG 2b K | 14.1 | 38.7 | 5.4 | 114.0 | 13.0 | 18.6 | 19.4 |
| SA5A1.1 | IgG 1 K | 74.0 | 83.1 | 60.0 | 2100.0 | 870.0 | 1200.0 | 1190.0 |

*The first two letters of each clone designate whether the immunizing hapten was atrazine-mecaptopropanoic acid (AM) or simazine-aminohexanoic acid (SA) conjugates.
**IC50 is the concentration of free triazine that half-maximally inhibited the competition ELISA. Values determined from four parameter fitted curves; ppb = parts/billion or ng/ml.

These results show that each triazine analog has a characteristic profile with respect to the 5-member antibody panel.

Example 2

Determination of CRIM Profiles

Figure 1B:
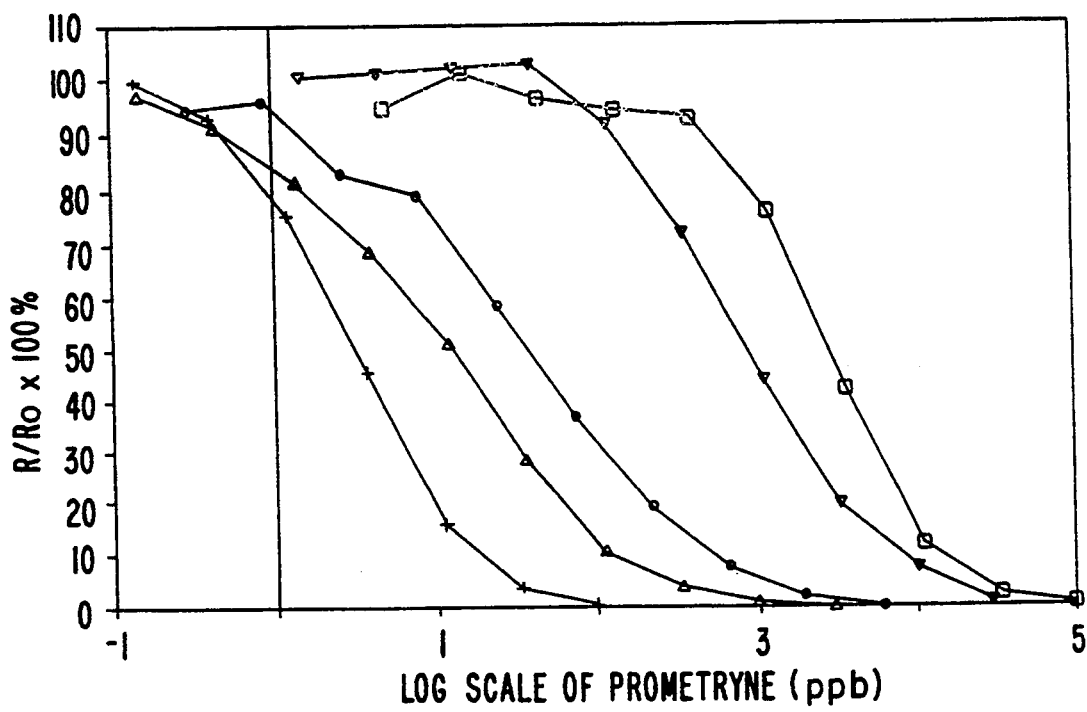
FIG. 1B shows patterns of inhibition of binding of a series of monoclonal antibodies to immobilized prometryne as a function of concentration of related antigens in solution.

A series of standard profiles for each triazine analog over the 10–1000 ppb range was calculated from the inhibition curves obtained for each of the analogs as exemplified in FIG. 1. The result of this theoretical calculation for 50 ppb is shown in FIG. 2B. As seen, the percentage inhibition patterns across the panels is distinctive for each individual analog.

Figure 2A:
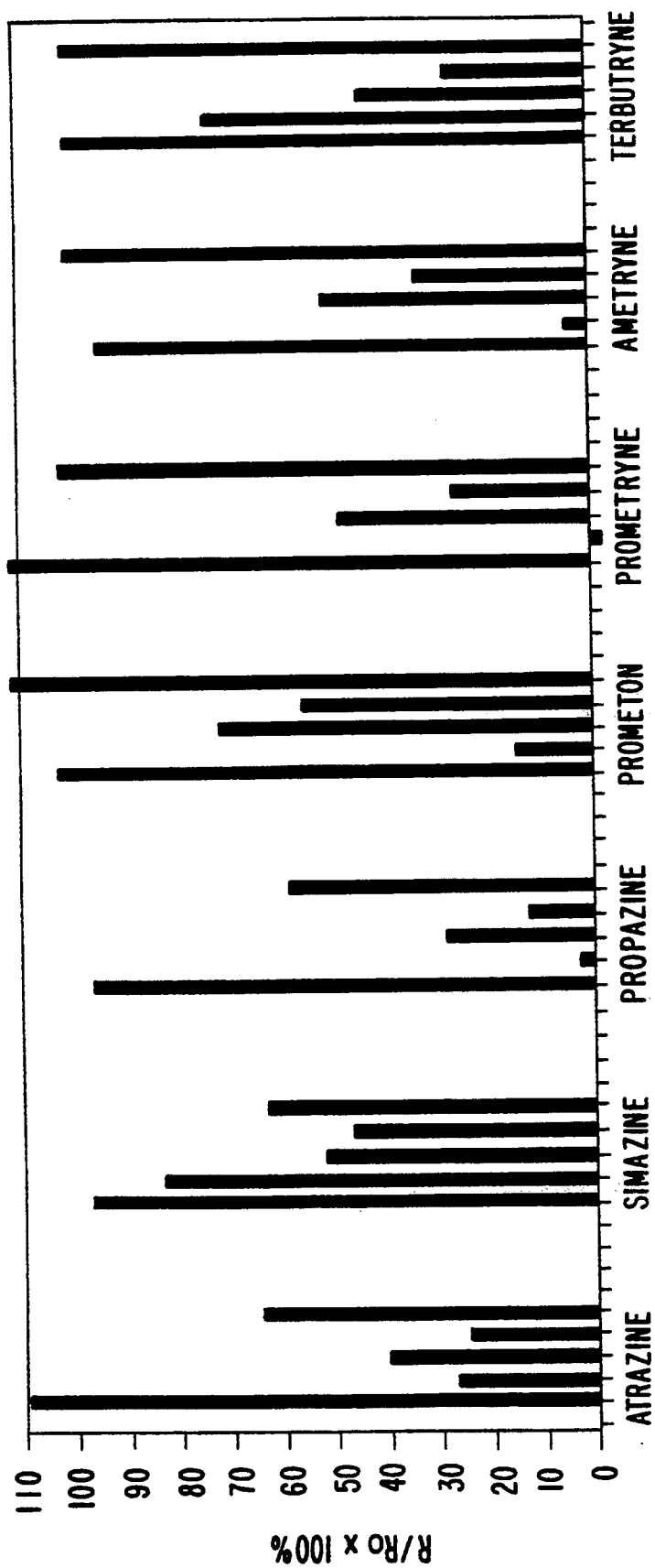
FIG. 2A shows the experimental cross-reaction immunoassay (CRIM) profiles for triazine homologs determined at 50 parts per billion (ppb).
Figure 2B:
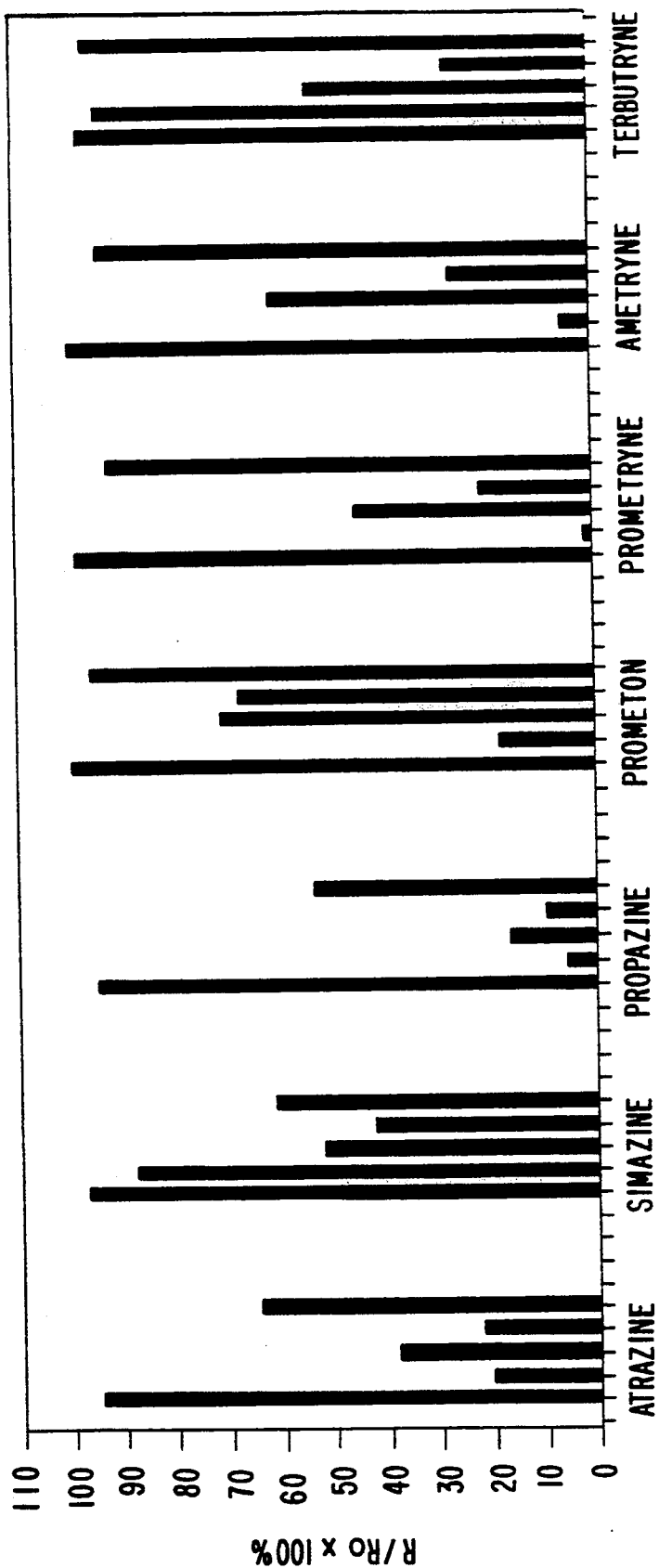
FIG. 2B shows predicted cross-reaction immunoassay (CRIM) profiles for triazine homologs determined at 50 parts per billion (ppb).

The profiles were also determined experimentally at 50 ppb, as shown in FIG. 2A. The calculated and experimental patterns are highly similar. The results shown graphically in FIG. 2A are given as numerical values in Table 3 below.

Matching experimental profiles to calculated reference profiles allows identification of unknown samples. A catalog of calculated profiles thus provides a reference for unknown sample determination.

TABLE 3

IMMUNO-CROSSREACTION PROFILES OF 7 S-TRIAZINES (AT 50 PPB) VS. 5 ANTI-TRIAZINE MABS
Activities are expressed as percent of zero-dose control +/− standard deviation (n = 3)

| | AM5C5.3 | AM1B5.1 | AM5D1.2 | AM7B2.1 | SA5A1.1 |
|---|---|---|---|---|---|
| ATRAZINE | 89.7 +/− 6.8 | 9.6 +/− 2.9 | 28.1 +/− 1.9 | 11.7 +/− 0.9 | 64.8 +/− 2.3 |
| SIMAZINE | 88.2 +/− 5.5 | 75.5 +/− 6.1 | 43.6 +/− 2.8 | 26.3 +/− 2.4 | 63.6 +/− 4.9 |
| PROMETRYN | 109.8 +/− 4.6 | 0.9 +/− 1.3 | 47.9 +/− 3.0 | 18.9 +/− 1.3 | 59.4 +/− 4.9 |
| PROMETON | 103.6 +/− 4.7 | 17.8 +/− 2.4 | 71.6 +/− 1.5 | 46.6 +/− 1.4 | 105.1 +/− 4.6 |
| PROPAZINE | 83.8 +/− 6.1 | 1.4 +/− 0.8 | 14.7 +/− 2.1 | 3.9 +/− 0.6 | 102.7 +/− 3.0 |
| AMETRYN | 91.8 +/− 1.8 | 6.2 +/− 1.1 | 44.0 +/− 2.4 | 27.0 +/− 1.0 | 100.9 +/− 3.8 |
| TERBUTRYN | 96.6 +/− 2.4 | 80.6 +/− 5.6 | 41.5 +/− 4.3 | 20.1 +/− 1.3 | 101.1 +/− 4.8 |

Determination of Composition/Reactivity Plot

Profiles such as those shown in FIG. 2A of Example 2 were determined for a series of concentrations of all seven triazines in the 10–1000 ppb range. The percent inhibition values for the five antibodies for each triazine at each concentration provides a coordinate in 5-dimensional space. Thus, each analog at each concentration gives a single point representing the profile in 5-dimensional space.

The resultant pattern shows a unique series of points represented by individual analytes at various concentrations with respect to the antibody panel.

Figure 3:
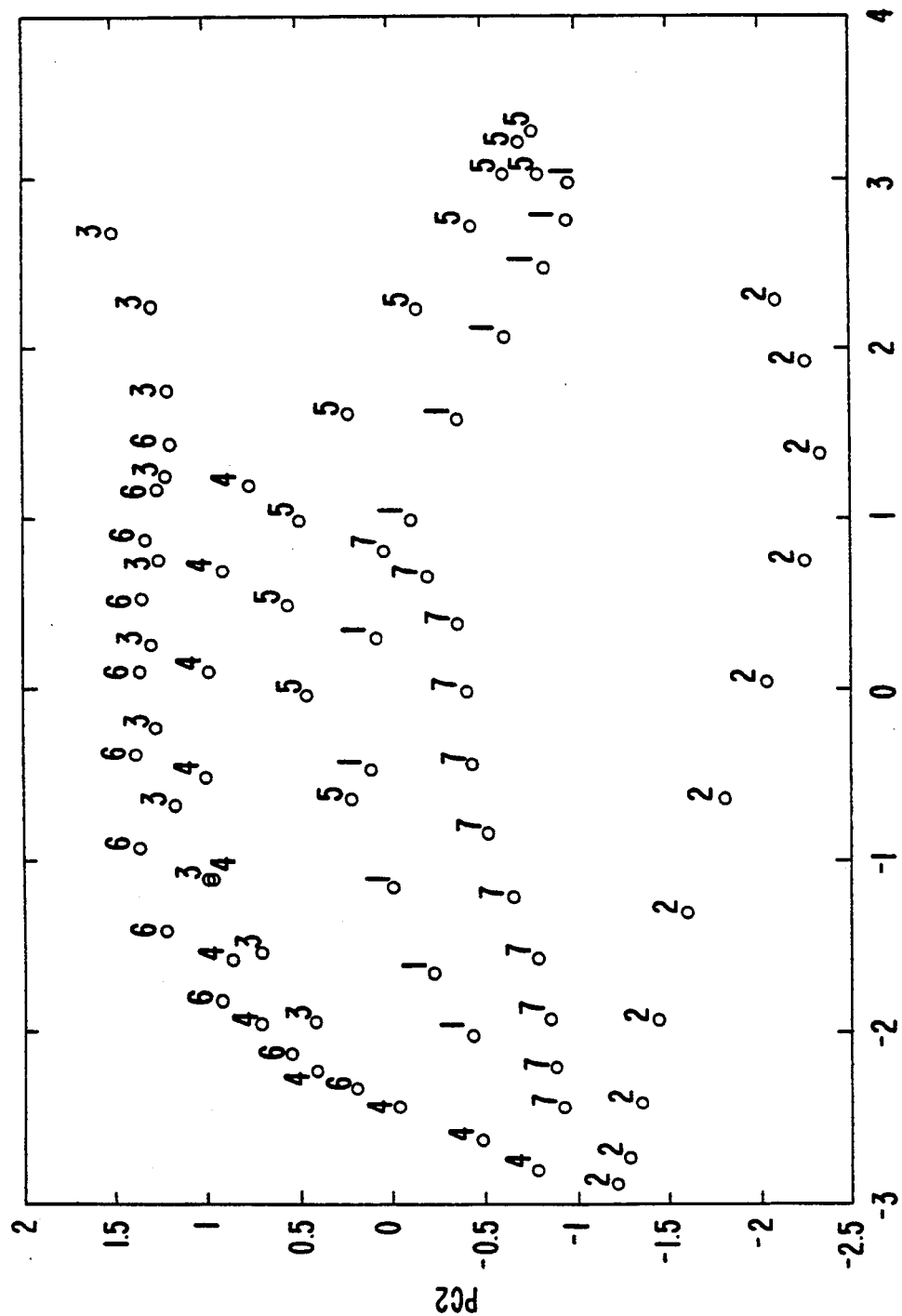
FIG. 3 shows an optimized two-dimensional projection of five-dimensional CRIM profiles for seven triazine herbicides at concentrations ranging from 10–1000 ppb.

In order to visualize these data better, the 5-dimensional plot is projected into a 2-dimensional array, as shown in FIG. 3.

The orientation of the two-dimensional plane used for this projection is that which best preserves the scatter of the data, i.e., which minimizes points lying on top of each other in the projection when they are well separated. This orientation is defined mathematically as the plane specified by the principal components of the data. Projecting points onto the plane defined by the principal components preserves the clustering and characteristics of the original data as described by Massart, D. L., et al., "Chemometrics: A Textbook" (1988) Elsevier, N.Y.

As shown in FIG. 3, all points labeled "1" represent various concentrations of atrazine, all points labeled "2" represent varying concentrations of simazine, and so forth.

By determining the point location resulting from obtaining the profile of a sample in the same manner as described for known compositions in this example, the analyte composition of the sample can be obtained.

We claim:

1. A method to identify analyte and to determine analyte concentration of a sample containing at least one member analyte of a set of analytes cross-reactive with at least two specific binding reagents, wherein said cross-reactive set of analytes contains at least 2 members, which method comprises:

1) contacting the sample with each specific binding reagent of a panel containing n specific binding reagents reactive with the members of the set wherein n is an integer and is at least 2;
2) measuring the binding affinity of each specific binding reagent in the panel with the sample;
3) recording each said binding affinity of each said binding reagent in said panel;
4) arranging said recorded binding affinities into a convenient pattern for comparison to obtain a cross-reactivity of specific binding reagents (CRSBR) profile of said sample; and
5) comparing said CRSBR profile thus obtained with a set of CRSBR reference profiles for individual member analytes and mixtures of member analytes thereby to find a matching CRSBR reference profile corresponding to a composition for which the identity and concentration of each said member analyte is known, wherein each CRSBR reference profile for an individual member analyte consists of binding affinities for all specific binding reagents of said panel against a single concentration of an individual member analyte arranged in said convenient pattern in a physical embodiment, and wherein each CRSBR reference profile for a mixture of said member analytes consists of binding affinities for all specific binding reagents of said panel against a single concentration of a single mixture of two or more member analytes arranged in said convenient pattern, said binding affinities for said single mixture being calculated by combining said recorded binding affinities for single concentrations of said individual member analytes.

2. The method of claim 1 wherein said comparing includes the steps of:

identifying point obtained by plotting, in n-dimensional space, the binding affinity of the sample for each specific binding reagent of the panel, wherein each n dimension represents a different specific binding reagent in the panel; and comparing the position of said point to predetermined points in said n-dimensional space for the CRSBR profiles of the reference set representing the binding affinity for each specific binding reagent of various concentrations of said member analytes contacted with said panel, thereby determining the analyte concentration of the sample.

3. The method of claim 1 wherein said comparing includes the steps of:

determining from the reference set the value of the concentration of each candidate analyte in said sample which corresponds to the binding affinity of the sample with each specific binding reagent of said panel so as to obtain a set of n determined concentrations for each candidate analyte; and identifying the analyte as that candidate which results in the most consistent concentration among said candidates across the n specific binding reagents of the panel.

4. The method of claim 3 which further includes weighting the results for each specific binding reagent by counting as more important binding affinities which correspond to the linear portion of the binding curve for said candidate with said specific binding reagent.

5. The method of claim 1 wherein said comparing includes providing the binding affinity for each specific binding reagent in said CRSBR profile for said sample to a neural net which has been trained by the reference set of CRSBR profiles.

6. The method of claim 1 wherein said cross-reactive set of analytes contains 2-20 members.

7. The method of claim 1 wherein said panel of specific binding reagents contains 2-10 specific binding reagents.

8. The method of claim 1 wherein said specific binding reagents are antibodies or immunologically reactive fragments thereof.

9. The method of claim 8 wherein said antibodies are single chain antibodies or recombinantly produced antibodies.

10. The method of claim 1 wherein said cross-reactive set of analytes is comprised of triazines.

11. A method to prepare a set of cross-reactivity of specific binding reagents (CRSBR) reference profiles for individual member analytes and mixtures of member analytes of a set of analytes cross-reactive with at least two specific binding reagents, wherein said cross-reactive set of analytes contains at least two members, which method comprises:

1) determining the binding affinity of each specific binding reagent of a panel containing n specific binding reagents reactive with each member analyte of said set, wherein n is an integer and is at least 2, for each individual member of said set of cross-reactive analytes at a series of known concentrations of each said member;

2) recording each said binding affinity of each said binding reagent with each said member analyte at each concentration in said series;

3) arranging said recorded binding affinities into CRSBR reference profiles for individual member analytes, each such reference profile consisting of binding affinities for all specific binding reagents of said panel with a single concentration of an individual member analyte arranged in a convenient pattern for comparison;

4) calculating binding affinities for CRSBR reference profiles for mixtures of said member analytes by combining said recorded binding affinities for single concentrations of said individual member analytes;

5) arranging said calculated binding affinities into CRSBR reference profiles for mixtures of said member analytes, each such reference profile consisting of binding affinities for all specific binding reagents of said panel against a single concentration of a single mixture of two or more member analytes arranged in said convenient pattern; and 6) storing the CRSBR reference profiles resulting from steps 3 and 5 in a physical embodiment, thereby providing said set of CRSBR reference profiles.

12. The method of claim 11 wherein the step of determining the affinity of each specific binding reagent in said panel for each member of said cross-reactive set of analytes at said series of concentrations is conducted by:

contacting a plurality of samples each having a different known concentration of a member analyte of said cross-reactive set with each of n specific binding reagents in said panel of specific binding reagents reactive with members of the set wherein n is an integer and is at least 2; and measuring the binding affinity of each specific binding reagent in the panel with each sample.

13. The method of claim 11 wherein the step of determining the binding affinity of each specific binding reagent in the panel for each member of said crossreactive set of analytes at a series of concentrations of said member is conducted by:

calculating a measure of said binding affinity at each concentration from an inhibition curve for said analyte with respect to said panel member.

14. The method of claim 11 wherein said cross-reactive set of analytes contains 2-20 members.

15. The method of claim 11 wherein the panel of specific binding reagents contains 2-10 members.

16. The method of claim 11 wherein the specific binding reagents are antibodies or immunologically reactive fragments thereof.

17. The method of claim 16 wherein the antibodies are single chain antibodies or recombinant antibodies.

18. The method of claim 11 wherein said set of cross-reactive analytes are triazines.

19. The method of claim 11 wherein said physical embodiment comprises a computationally accessible form of said set of CRSBR reference profiles.

20. The computationally accessible reference set of CRSBR profiles obtained by the method of claim 19.

21. The method of claim 19 wherein said computationally accessible form is a pattern of points in n-dimensional space wherein each of said n dimensions represents a different specific binding reagent of the panel obtained by identifying the points obtained by plotting the binding affinity for each concentration of each analyte with each of said n specific binding reagents in n-dimensional space;

thus obtaining said pattern of points representing known analyte concentrations in n-dimensional space.

22. The pattern obtained by the method of claim 21.

23. The method of claim 21 which further comprises projecting said pattern into a space of less than n dimensions to obtain a more computationally tractable representation of said known concentrations.

24. The method of claim 23 wherein said computational representation of less than n dimensions is specified by the principal components of the data, wherein said data are said binding affinities.

25. The computational representation of less than n dimensions obtained by the method of claim 23.

26. The computational representation of less than n dimensions of claim 25 which is a two-dimensional plot.

* * * * *